US00PP15836P2

(12) United States Plant Patent
Kobayashi

(10) Patent No.: US PP15,836 P2
(45) Date of Patent: Jul. 5, 2005

(54) ***POINSETTIA* PLANT NAMED 'WINCREA'**

(50) Latin Name: *Euphorbia pulcherrima*
Varietal Denomination: Wincrea

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 10/859,515

(22) Filed: Jun. 1, 2004

(51) Int. Cl.[7] ..... A01H 5/00
(52) U.S. Cl. ..... Plt./305
(58) Field of Search ..... Plt./305, 304

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Poinsettia* plant named 'Wincrea', characterized by its ball-shaped inflorescences with recurved pale yellow-colored flower bracts; recurved dark green-colored leaves; uniform plant habit; and excellent postproduction longevity.

1 Drawing Sheet

Botanical classification/cultivar designation: *Euphorbia pulcherrima* Willd. cultivar Wincrea.

BACKGROUND OF THE INVENTION

The present Invention relates to a new and distinct cultivar of *Poinsettia* plant, botanically known as *Euphorbia pulcherrima* Willd., and hereinafter referred to by the name 'Wincrea'.

The new *Poinsettia* a product of a planned breeding program conducted by the Inventor in Encinitas, Calif. The objective of the breeding program is to create new *Poinsettia* cultivars having strong stems, reflexed flower bracts with desirable colors, uniform plant habit and excellent post-production longevity.

The new *Poinsettia* is a naturally-occurring branch mutation of the *Euphorbia pulcherrima* Willd. cultivar Eckalbeno, disclosed in U.S. Plant Pat. No. 13,316. The new *Poinsettia* was discovered and selected by the Inventor within a population of plants of the cultivar Eckalbeno in November, 2000, in a controlled environment in Encinitas, Calif. The selection of this plant was based on its strong stems and reflexed pale yellow-colored flower bracts.

Asexual reproduction of the new *Poinsettia* by terminal cuttings propagated in a controlled environment in Encinitas, Calif., since January, 2001, has shown that the unique features of this new *Poinsettia* are stable and reproduced true to type in successive generations of asexual reproduction.

BRIEF SUMMARY OF THE INVENTION

The following traits have been repeatedly observed and are determined to be the unique characteristics of 'Wincrea'. These characteristics in combination distinguish 'Wincrea' as a new and distinct cultivar:

1. Ball-shaped inflorescences with recurved pale yellow-colored flower bracts.
2. Recurved dark green-colored leaves.
3. Uniform plant habit.
4. Strong erect stems.
5. Response time about 8.5 weeks.
6. Excellent post-production longevity.

Plants of the new *Poinsettia* are most similar to the parent, the cultivar Eckalbeno. Plants of the new *Poinsettia* differ primarily from plants of the parent in flower bract coloration as plants of the cultivar Eckalbeno have pink and pale yellow bi-colored flower bracts.

Plants of the new *Poinsettia* can be compared to plants of the cultivar Eckaimon, disclosed in U.S. Plant Pat. No. 13,909. In side-by-side comparisons conducted in Encinitas, Calif., plants of the new *Poinsettia* differed from plants of the cultivar Eckaimon in the following characteristics:

1. Plants of the new *Poinsettia* were shorter than plants of the cultivar Eckaimon.
2. Plants of the new *Poinsettia* were more freely branching than plants of the cultivar Eckaimon.
3. Plants of the new *Poinsettia* flowered about three or four days earlier than plants of the cultivar Eckaimon.
4. Plants of the new *Poinsettia* had smaller inflorescences than plants of the cultivar Eckaimon.

BRIEF DESCRIPTION OF THE PHOTOGRAPHS

The accompanying colored photographs illustrate the overall appearance of the new *Poinsettia*, showing the colors as true as it is reasonably possible to obtain in colored reproductions of this type. Colors in the photographs may differ slightly from the color values cited in the detailed botanical description which accurately describe the colors of the new *Poinsettia*.

The photograph at the top of the sheet comprises a side perspective view of a typical flowering plant of 'Wincrea'.

The photograph at bottom left of the sheet is a close-up view of a typical inflorescence of 'Wincrea'.

The photograph at the bottom right of the sheet is a top perspective view of a typical flowering plant of 'Wincrea'.

DETAILED BOTANICAL DESCRIPTION

The new *Poinsettia* has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the autumn and winter under commercial practice in a polyethylene-covered greenhouse with day temperatures about 24° C., night temperatures about 19° C., and light levels about 4,000 foot-candles. Single plants were grown in 16.5-cm pots and pinched once. Plants were flowered under natural season short day/long night conditions. Plants were about 17 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Wincrea.

Parentage: Naturally-occurring branch mutation of *Euphorbia pulcherrima* Willd. cultivar Eckalbeno, disclosed in U.S. Plant Pat. No. 13,316.

Propagation:

*Type cutting.*—Terminal cuttings.

*Time to initiate roots.*—About ten days at 20 to 22° C.

*Time to develop roots.*—About four weeks at 24° C.

*Root description.*—Thick, fibrous and freely-branching.

Plant description:

*Plant form.*—Inverted triangle; strong and erect stems.

*Growth habit.*—Upright and uniform plant habit. Moderately vigorous.

*Plant height.*—About 23 cm.

*Plant diameter or spread.*—About 30 cm.

*Lateral branch description.*—Quantity: About eight lateral branches develop after pinching. Length: About 18 cm. Diameter: About 6 mm. Internode length: About 2.3 cm. Strength: Strong, stiff. Texture: Smooth; glabrous. Color: 146B.

*Foliage description.*—Arrangement: Alternate, single. Length: About 10.5 cm. Width: About 7.5 cm. Shape: Roughly elliptic. Apex: Acuminate. Base: Obtuse to truncate. Margin: Entire; somewhat sinuate. Venation pattern: Pinnate. Texture, upper and lower surfaces: Glabrous; slightly rugose. Orientation: Recurved. Color: Developing and fully expanded foliage, upper surface: Darker than 147A. Developing and fully expanded foliage, lower surface: More gray than 147B. Venation, upper and lower surfaces: 147B. Petiole: Length: About 1.6 cm. Diameter: About 3 mm. Texture, upper and lower surfaces: Smooth; glabrous. Color: 146B.

Inflorescence description:

*Inflorescence type and habit.*—Inflorescences are compound corymbs of cyathia with colored flower bracts subtending the cyathia. One inflorescence per lateral branch. Flower bracts recurved, inflorescences ball-shaped. Flowers are not fragrant. Flowers persistent.

*Natural flowering season.*—Autumn/winter in Northern Hemisphere. Flower initiation and development is induced under long nyctoperiod conditions. Response time, about 8.5 weeks; natural season flower maturity date is late November for plants grown in Encinitas, Calif.

*Post-production longevity.*—Plants of the new Poinsettia maintain good substance and bract color for about four weeks under interior conditions.

*Inflorescence size.*—Diameter: About 10 cm. Height (depth): About 4.5 cm.

*Flower bracts.*—Quantity per inflorescence: About 20. Length, largest bracts: About 8 cm. Width, largest bracts: About 7.2 cm. Shape: Elliptic. Apex: Acuminate, curled. Base: Obtuse. Margin: Entire; slightly sinuate. Texture, upper and lower surfaces: Glabrous; velvety; rugose. Orientation: Recurved. Venation pattern: Pinnate. Color: Developing or transitional bracts, upper surface: 10B. Developing or transitional bracts, lower surface: 10C. Fully developed bracts, upper and lower surfaces: 5D. Venation, upper and lower surfaces: Similar to flower bract color. Bract petiole: Length: About 1.5 cm. Diameter: About 2 mm. Texture, upper and lower surfaces: Smooth; glabrous. Color: 144A.

*Cyathia.*—Quantity: About eight per corymb. Diameter of cyathia cluster. About 2 cm. Length: About 8 mm. Width: About 5 mm. Shape: Ovoid. Color, immature and mature: 144B. Peduncle: Length: About 1 mm. Diameter: About 2 mm. Strength: Strong. Aspect: Mostly upright. Texture: Smooth; glabrous. Color: 144B. Stamens: Quantity per cyathium: About five. Anther shape: Bilobed. Anther length: About 1 mm. Anther color: 13B. Amount of pollen: Scarce. Pollen color: 13B. Pistils: None observed. Nectaries: Quantity per cyathium: One. Size: About 3 mm by 5 mm. Color: 13A.

Disease/pest resistance: Resistance to pathogens and pests common to *Poinsettias* has not been observed on plants grown under commercial conditions.

It is claimed:

1. A new and distinct cultivar of *Poinsettia* plant named 'Wincrea', as illustrated and described.

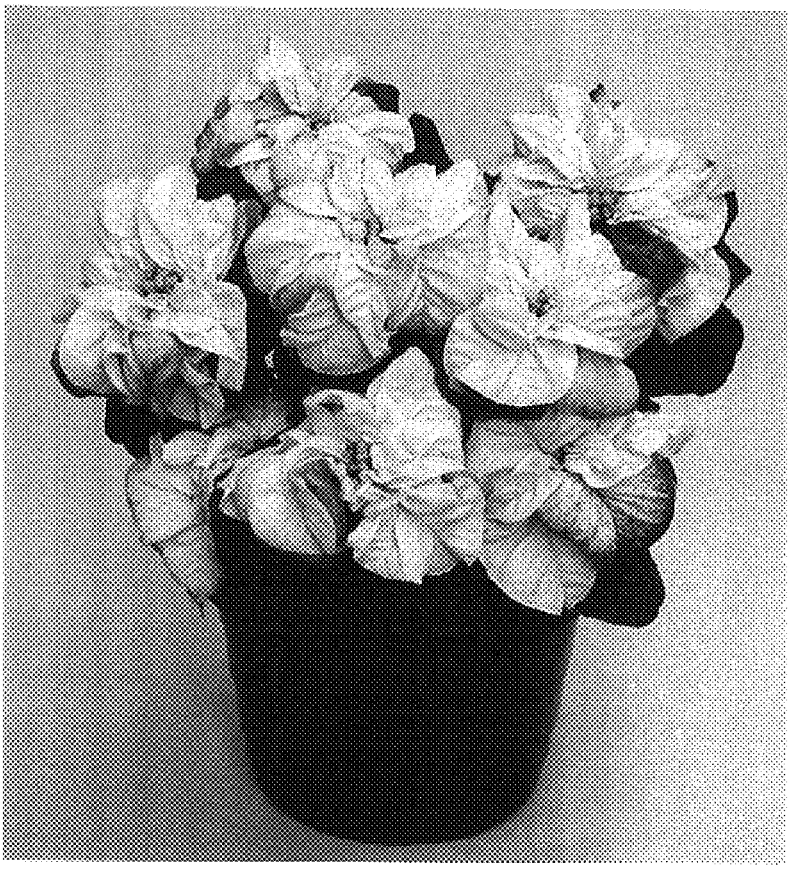
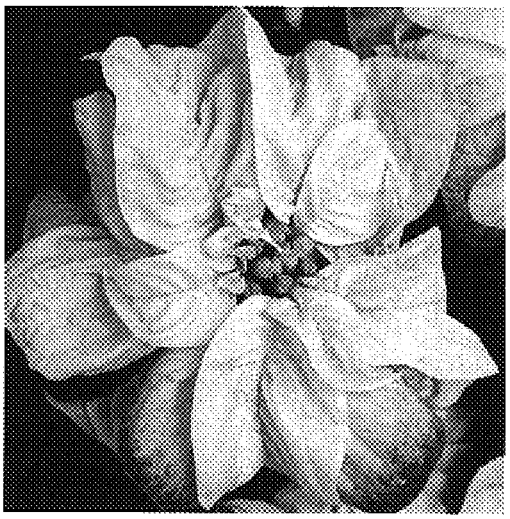
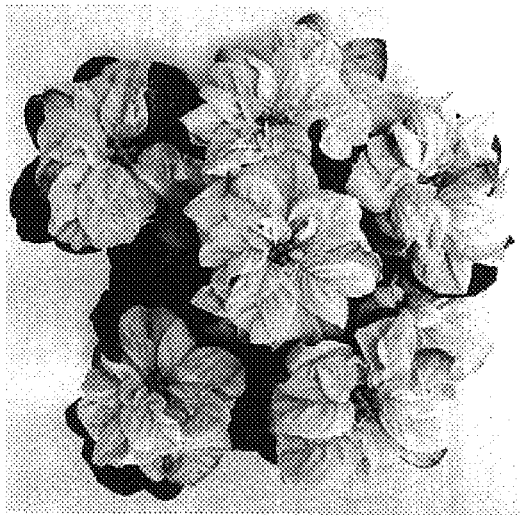

* * * * *